United States Patent
Palazzo et al.

[11] Patent Number: 6,062,223
[45] Date of Patent: May 16, 2000

[54] TRACHEAL TUBE DEVICES

[76] Inventors: Mark George Anthony Palazzo, 32 Holst Mansions, Wyatt Drive, Barnes, London SW13 8AJ; Neil Soni, 164 Court Lane, Dulwich, London SE21, both of United Kingdom

[21] Appl. No.: 09/144,465

[22] Filed: Sep. 1, 1998

[30]  Foreign Application Priority Data

Sep. 1, 1997 [GB] United Kingdom .................... 9718534

[51] Int. Cl.⁷ ................................................. A61M 16/00
[52] U.S. Cl. ................................ 128/207.15; 128/207.14
[58] Field of Search ......................... 128/207.14, 207.15; 604/101, 103

[56] References Cited

U.S. PATENT DOCUMENTS

| | | | |
|---|---|---|---|
| 4,091,816 | 5/1978 | Elam | 604/101 |
| 4,156,428 | 5/1979 | Henkin | 128/207.15 |
| 4,235,239 | 11/1980 | Elam | 128/207.15 |
| 4,305,392 | 12/1981 | Chester | 128/207.15 |
| 4,327,721 | 5/1982 | Goldin et al. | 128/207.15 |
| 4,341,210 | 7/1982 | Elam | 128/207.15 |
| 4,351,330 | 9/1982 | Scarberry | 128/207.15 |
| 4,402,319 | 9/1983 | Handa et al. | 604/103 |
| 4,423,725 | 1/1984 | Baran et al. | 128/207.15 |
| 4,538,606 | 9/1985 | Whited | 128/207.15 |
| 4,700,700 | 10/1987 | Eliachar | 604/101 |
| 4,840,173 | 6/1989 | Porter, III | 128/207.15 |
| 4,976,261 | 12/1990 | Gluck et al. | 604/103 |
| 4,979,505 | 12/1990 | Cox | 128/207.15 |
| 5,033,466 | 7/1991 | Weymuller, Jr. | 128/207.15 |
| 5,060,647 | 10/1991 | Alessi | 128/207.15 |
| 5,201,310 | 4/1993 | Turnbull | 128/207.15 |
| 5,311,864 | 5/1994 | Huerta | 128/207.15 |
| 5,318,021 | 6/1994 | Alessi | 128/207.15 |
| 5,507,284 | 4/1996 | Daneshvar | 128/207.15 |
| 5,819,733 | 10/1998 | Bertram | 604/101 |

FOREIGN PATENT DOCUMENTS

| | | |
|---|---|---|
| 0 490 852 | 6/1992 | European Pat. Off. . |
| 39 19 634 | 12/1990 | Germany . |
| 693510 | 7/1953 | United Kingdom . |
| 2250440 | 6/1992 | United Kingdom . |
| WO 97/23163 | 7/1997 | WIPO . |

*Primary Examiner*—Aaron J. Lewis
*Attorney, Agent, or Firm*—Pollock, Vande Sande & Amernick

[57]  ABSTRACT

An endotracheal tube 10 has an inflatable bag 20 towards its patient end for sealing with the inside of the trachea 11. Additionally, the tube 10 has a second, longer bag 50 separately inflatable to a lower pressure than the first bag 20 and such as to extend along the tube 10 from the first bag 20 to and through the vocal chords and larynx 13 and occupy the space between the first bag and the vocal chords 13. The inflated second tube 50 can thus reduce passage of secretions and minimizes the space available for them. A suction line 48 extends along the tube, opening between, or at the interface between, the two bags 20 and 50 so that any body secretions that do pass the second bag can be removed.

7 Claims, 2 Drawing Sheets

TRACHEAL TUBE DEVICES

BACKGROUND OF THE INVENTION

This invention relates to tracheal tube devices of the kind for insertion into the trachea, the device comprising a main tube encompassed towards its distal end by an inflatable bag and, extending to the interior of the bag, an inflation line by which the bag can be inflated. Generally, the inflatable bag is a cuff or a balloon.

A common feature of tracheal tube devices of this kind, such as endotracheal or tracheostomy tubes, is that bodily secretions, mucous, or other unwanted fluids can collect in the cusp between the inner surface of the body conduit and the ovate upstream surface of the inflated cuff or balloon. These bodily secretions often pass progressively between the inner surface of the trachea and the outer surface of the cuff or balloon—even though these surfaces are supposed to be in mutually sealing contact. These bodily secretions can pass from the trachea and enter the bronchi, potentially to cause lung infections. This passage of unwanted fluids past the inflated bag of the tracheal tube device is thought to be due to the patient's breathing cycle producing fluctuating inhalation/exhalation pressures on the downstream ovate surface of the inflated bag and causing the latter and/or the tracheal conduit to act somewhat in the manner of a peristaltic pump.

One proposed solution to this problem is to provide the tube device, not only with an inflation line to the distal bag but also with a suction line opening to a region above the bag. In practice however, due to the finite axial length accommodated by the tape or other fastening means required to attach the bag sealingly to the main tube of the structure, the opening from the suction line is disposed too far above the upstream ovate surface of the bag to ensure removal by suction of all the unwanted fluids collecting in that region. Even where the collar of the bag is everted, in the manner described in GB-2250440, suction may not ensure complete removal of all secretions.

It is thus clearly desirable to provide an improved tracheal tube device.

SUMMARY OF THE INVENTION

According to the present invention there is provided a tracheal tube device for insertion into the trachea, the device comprising:

a main tube encompassed towards its distal end by a first inflatable bag;

an inflation line extending to the interior of the first bag by which the first bag can be inflated; and a second bag to encompass the main tube; characterized in that the device includes a second inflation line by which the second bag can be inflated separately from the first bag, and in that the second inflatable bag is dimensioned and arranged in use to occupy the space from the first inflatable bag—i.e. between contact with or close proximity to the first inflatable bag—to at least the patient's vocal chords.

Preferably, the second bag extends through the vocal chords. The second bag may be about three time the length of the first bag. The second bag is preferably inflated in use to a lower pressure than the first bag, such as between about 2 and 5 cm water. The device may include a suction line extending from the proximal end of the device and opening on the main tube at a location between the first and second bags. The first bag may have an upper surface shaped to form a receptacle for the collection of fluids. The second bag may be a cuff attached at its ends with the main tube or it may be a balloon that encompasses the wall of the main tube, in which case, the second bag may be slidable along the main tube. Advantageously, the lower end of the second bag, when inflated, nests within the receptacle provided by the upper surface of the first bag, when inflated.

According to another aspect of this invention there is provided a method of intubation into the trachea of an animal or human patient a tracheal tube device having the foregoing construction, comprising the steps of:

inserting the main tube and first inflatable bag through the larynx into the trachea to dispose the first bag in spaced relation to the larynx, inflating the first bag via the first inflation line, providing the second inflatable bag between the first bag and the larynx such that, when inflated, the second bag may contact or closely approach the first bag, and inflating the second bag to be in contact with or closely approach the first bag and occupy the space between the first bag and the larynx, preferably to extend through the larynx.

Advantageously, the first bag is inflated to a first pressure, and the second bag is inflated to a second pressure lower than the first pressure.

BRIEF DESCRIPTION OF THE DRAWINGS

By way of example, embodiments of this invention will now be described with reference to the accompanying drawings of which:

FIG. 3 is a partly cut-away generalized view of an endotracheal tube according to a second embodiment of this invention.

DESCRIPTION OF THE PREFERRED EMBODIMENTS

Figure 1:
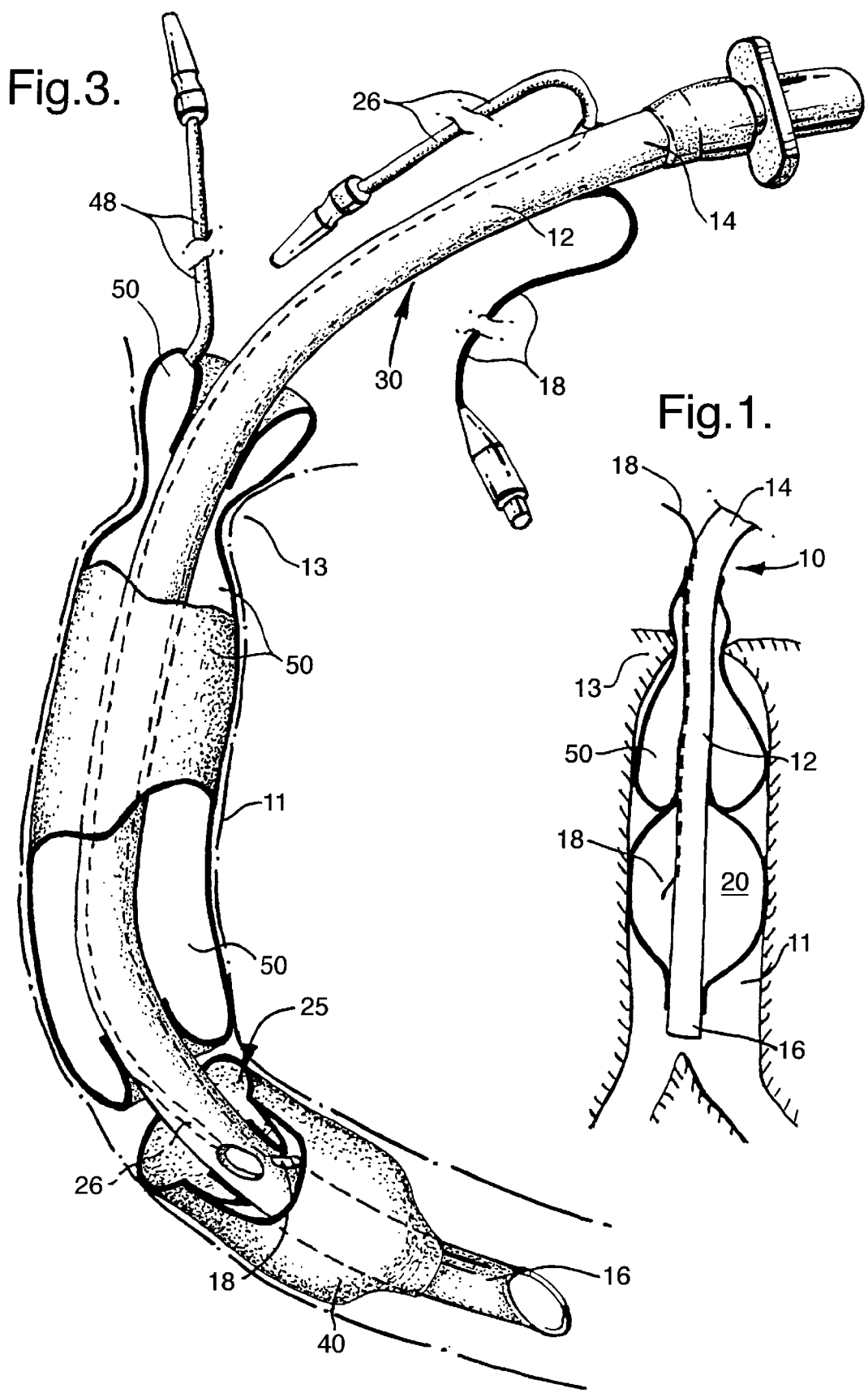
FIG. 1 is a schematic longitudinal section of an endotracheal tube according to one embodiment of this invention.
Figure 2:
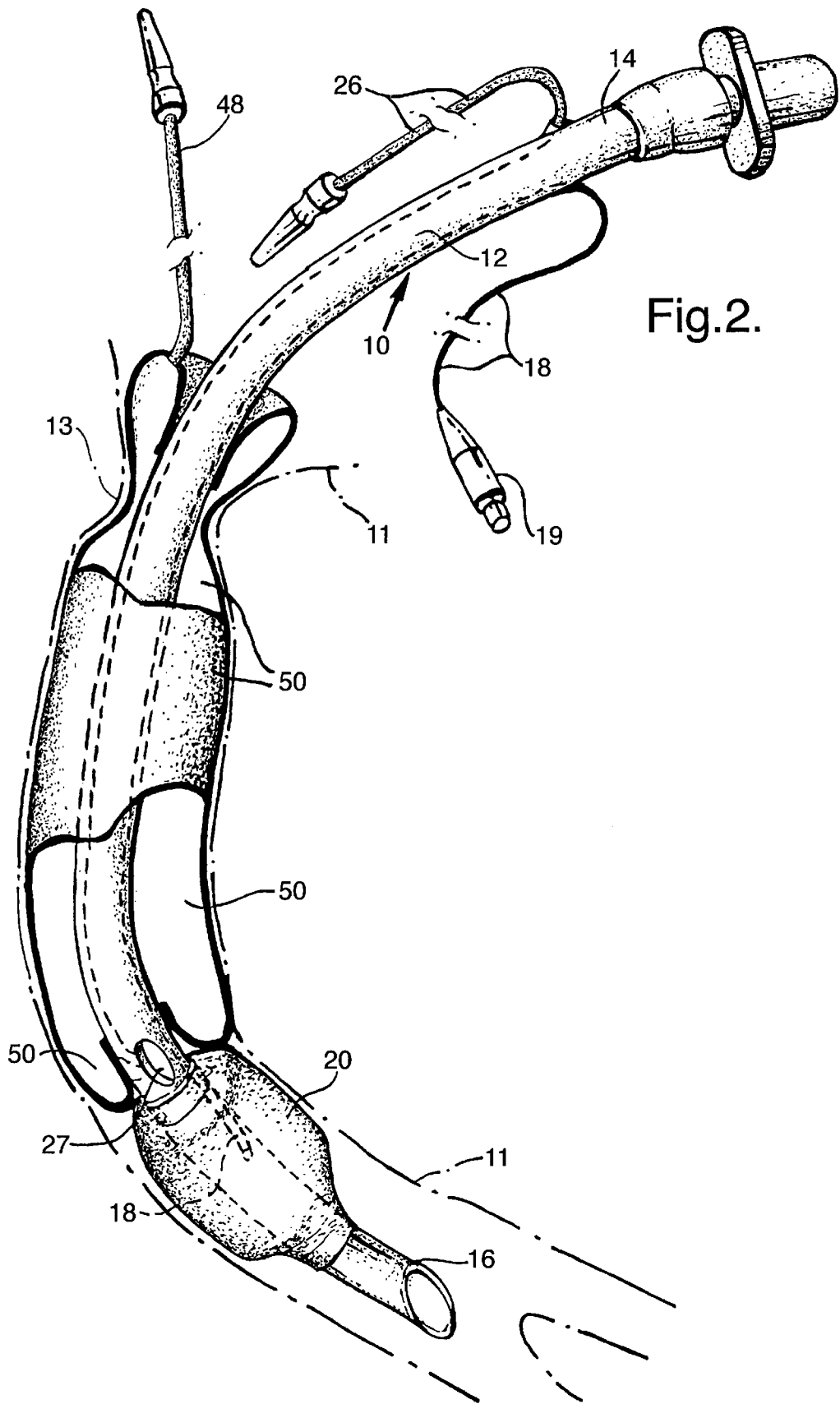
FIG. 2 is a partly cut-away generalized view of the embodiment of FIG. 1.

The illustrated endotracheal tube device 10 of FIGS. 1 and 2 is a tubular structure for insertion into a human or animal trachea 11 via the mouth or nose. The device 10 incorporates a substantially conventional endotracheal tube which comprises a main tube 12 with an axial bore, the tube having a proximal or machine end 14 and a distal or patient end 16 with an inflatable bag 20 encompassing the main tube adjacent the distal end 16. The device also has a second bag 50 to be described in detail below.

An inflation line 18 leads to the interior of the bag 20 to enable it to be inflated with air to a generally ovate-shape. The inflation line 18 is attached or integrally moulded with the wall of main tube 12 for the majority of its length such as to be internally (or externally) bonded to, or extruded integrally with, the wall of main tube 12. The proximal end of the inflation line 18 is provided with a spring-loaded valve 19 (FIG. 2) that is normally closed but is opened by insertion of a syringe (not shown) that is used to inflate the bag 20.

A suction line 26 is attached or integrally moulded with the wall of main tube 12 for the majority of its length such as to be externally (or internally) bonded to, or extruded integrally with, the wall of main tube 12. This suction line 26 extends a position to adjacent the top surface of bag 20 where it terminates in an orifice 27 that opens on the exterior surface of the tube 12, so that unwanted fluids that may collect above the bag 20 can be removed by suction.

The bag 20 may be provided by a cuff adhered at its ends to the exterior surface of main tube 12 so that the bag is defined by the cuff material and the main tube's exterior surface between the cuffs ends.

Alternatively, the bag 20 may be provided by a balloon of generally toroidal extent encompassing the main tube 12 and having the balloon's radially inner surface adhered to the exterior surface of the main tube 12.

As stated above, the endotracheal tube device 10 of this embodiment also comprises a second bag 50. This is located between the first inflatable bag 20 and the proximal end 14 of the main tube 12, the bag 50 being separately inflatable via a second inflation line 48 and such that the two bags 20,50 (when inflated) are in contact with or very closely approach one another. The second bag 50 is substantially longer than the first, distal bag 20, typically being about three times its length. The length of the second bag 50 is chosen so that it occupies substantially all of the space between the first bag 20 and the vocal chords 13, and preferably extends through and above the vocal chords 13 by a short distance when the patient end 16 of the tube is correctly located, just above the patient's carina.

In use, following insertion of the endotracheal tube 10 into the patient's trachea, the first bag 20—which is located spaced from the patient's vocal chords 13—is inflated to provide a seal against the trachea 11, and the second bag 50 is then inflated so as to occupy all or at least the majority of the space or volume between the inflated first bag 20 and the larynx, or vocal chords 13.

In this way, the bag 50 minimizes the trachea volume available above the bag 20 in which unwanted fluids can collect. It thus prevents or minimizes the quantity of such unwanted fluids that can exist above the bag 20 and that could travel past this bag 20 into the patient's lungs.

When the tube device 10 is to be extubated from the patient, the bag 50 is deflated first and, before deflating the lower bag 20, any minimal unwanted fluids collecting above bag 20 can (continue to) be removed via suction line 26.

The embodiment of FIG. 3 provides an endotracheal tube device 30 for insertion, via the nose or mouth, into a human or animal trachea 11. The endotracheal tube device 30 is similar to that of FIGS. 1 and 2 except that its main tube 12 is encompassed at its distal end 16 by an inflatable bag 40 of different shape from that of the bag 20 in FIGS. 1 and 2. Instead of being a conventional, wholly ovate bag as shown in FIGS. 1 and 2, the bag 40 of FIG. 3 has a shape to form (when inflated) a receptacle-like upper surface.

The bag 40 is shaped and/or attached to the outer wall surface of main tube 12, e.g. by tapes, adhesive, welding or the like, such that part of the inflated bag's exterior surface forms a receptacle 25 that encompasses the main tube 12 and defines therewith a space for the collection of unwanted fluids. This space is akin to a cup-shaped recess or depression formed inwardly of the body of the inflated bag at its end facing the tube's proximal end—as though that end's surface had been depressed inwards of the body of the inflated bag.

Depending on the size and shape of the bag 40, it is envisaged that the height of that bag's outer surface—which, when inflated, is in sealing contact with the trachea surface 11—may be approximately 2 cm to 6 cm, whereas the height of that bag's inner surface in contact with the exterior surface of the main tube 12 may be approximately 0.5 cm to 1.5 cm where the bag is a cuff, or substantially more where the bag is a balloon. However, in either case, the depth of the receptacle 25 formed by (and between) the inflated bag's exterior surface and the main tube 12 (i.e. the distance between its mouth and its bottom) may, for example, be 2 to 4 cm.

In use, the endotracheal tube device 30 is inserted into the patient's trachea to locate bag 40 spaced from the patient's larynx 13. Following insertion the bag 40 is inflated to provide a seal against the trachea 11, and the second bag 50 of device 30 is then inflated so as to extend from the inflated first bag 40—into the receptacle 25 of which the lower end of second bag 50 nestingly projects—and occupy the majority of the space or volume between the first inflatable bag 40 and the larynx, or vocal chords 13. In this way, the bag 50 minimizes the trachea volume available above bag 40 in which unwanted fluids can collect. It thus prevents or minimizes the quantity of such unwanted fluids that can exist above bag 40 and that could travel past the bag 40 into the patient's lungs.

It will be appreciated that with either of the embodiments of FIGS. 1 to 3, the dimensions of the bag 50 are preferably such that bag 50 encompasses upper regions of the main tube 12 and extends past the vocal chords of the human or animal patient. To avoid damage to the vocal chords and/or undue patient discomfort, the second bag 50 is inflated to a pressure substantially less than that of the lower bag 20 or 40. For example, the bag 20 or 40 may be inflated to a pressure of water of approximately 15 cm, whereas the second bag 50 may be inflated to a pressure of water of approximately only 2 cm to 5 cm.

The bag 50 may be either a cuff or a balloon that is permanently attached to the main tube 12. Alternatively, the bag 50 may be a separate balloon that, either after or prior to being fully inflated, is slid down the main tube 12 from the main tube's proximal end 14, and, the main tube is in position in the trachea with the first bag 20 or 40, the second bag 50 is then appropriately fully inflated.

Although the above-described and illustrated embodiments of this invention have been endotracheal tubes, the present invention is considered applicable also to other tracheal devices, such as tracheostomy tubes. Furthermore it will be appreciated that other modifications and embodiments of the invention, which will be readily apparent to those skilled in this art, are to be deemed within the ambit and scope of the invention, and the particular embodiments hereinbefore described may be varied in construction and detail, e.g. interchanging (where appropriate or desired) different features of each, without departing from the scope of the patent monopoly hereby sought.

Having thus described our invention, we claim:

1. A tracheal tube device for insertion into a patient's trachea, the device comprising:
   a main tube having a distal end and encompassed towards said distal end by a first bag;
   an inflation line extending to the interior of said first bag by which the first bag can be inflated to seal with such a patient's trachea around said main tube; and
   a second bag, slidable along the main tube after the main tube and the first bag have been inserted into such a patient's trachea, said second bag encompassing said main tube when in use;
   the device including a second inflation line by which the second bag can be inflated separately from the first bag to seal with said patient's trachea around said main tube at the same time that said first bag seals with such a patient's trachea around said main tube;

the second bag being dimensioned and arranged in use to occupy, when inflated, substantially the entire space around the outside of the main tube from the first bag when inflated to at least such a patient's vocal chords;

and the device including a suction line which extends from a proximal end of the device and opens on the main tube at a location between the first and second bags.

2. A tracheal tube device for insertion into a patient's trachea, the device comprising:

a main tube having a distal end and encompassed towards said distal end by a first bag;

an inflation line extending to the interior of said first bag by which the first bag can be inflated to seal with such a patient's trachea around said main tube; and a second bag which at least in use also encompasses said main tube;

the device including a second inflator line by which the second bag can be inflated separately from the first bag to seal with such a patient's trachea around said main tube at the same time that said first bag seals with such a patient's trachea around said main tube;

the second bag being dimensioned and arranged in use to occupy, when inflated, substantially the entire space around the outside of the main tube from the first bag when inflated to at least such a patient's vocal chords;

the device including a suction line which extends from a proximal end of the device and opens on the main tube at a location between the first and second bags;

wherein the first bag, when inflated, presents an upper surface that forms a receptacle;

and wherein the second bag, when inflated, presents a lower surface that nestingly projects into said receptacle formed by the first bag.

3. A device according to claim 1 or 2, wherein the second bag extends through such a patient's vocal chords when in use.

4. A method of intubating into the trachea of an animal or human patient a tracheal tube device having a main tube encompassed towards its distal end by a first bag, a first inflation line extending to the interior of the first bag by which the first bag can be inflated to present an upper surface that forms a receptacle and to seal with the trachea around the tube, a second bag which at least in use, also encompasses the main tube, a second inflator line by which the second bag can be inflated separately from the first bag to seal with the trachea around the main tube at the same time that said first bag, when inflated, seals with the trachea, said second bag being dimensioned and arranged in use to present, when inflated, a lower surface that nestingly projects into said receptacle formed by the first bag, when inflated, and to occupy substantially the entire space around the outside of the main tube between the first inflatable bag and at least the patient's vocal chords, and a suction line extending from a proximal end of the device and opening on said main tube at a location between the first and second bags;

said method comprising the steps of:

inserting said main tube and first bag through the patient's larynx into the trachea to dispose the first bag in spaced relation to the larynx;

inflating the first bag via said first inflation line to seal with the trachea around the main tube and form said receptacle;

positioning the second inflatable bag between the first bag and the larynx such that, when inflated, the second bag may contact or closely approach the first bag;

inflating the second bag to occupy substantially the entire space around the outside of the main tube between the first bag and the larynx and to be in contact with or closely approaching the first bag and with a lower surface thereof nestingly projecting into said receptacle formed by the first bag; and applying suction to said suction line to remove secretions from a location between the first and second bags.

5. A method according to claim 4 wherein the second inflatable bag is positioned to extend through the larynx.

6. A method according to claim 4 or claim 5, wherein the first bag is inflated to a first pressure, and the second bag is inflated to a second pressure lower than the first pressure.

7. A method of intubating into the trachea of an animal or human patient a tracheal tube device having a main tube encompassed towards its distal end by a first inflatable bag, a first inflation line extending to the interior of the first bag by which the first bag can be inflated to seal with the trachea around the tube, a second bag which at least in use, also encompasses the main tube, a second inflation line by which the second bag can be inflated separately from the first bag to seal with the trachea around the main tube at the same time that said first bag seals with the trachea, said second inflatable bag being dimensioned and arranged in use to occupy substantially the entire space around the outside of the main tube between the first inflatable bag and at least the patient's vocal chords, and a suction line extending from a proximal end of the device and opening on said main tube at a location between the first and second bags;

said method comprising the steps of:

inserting said main tube and first inflatable bag through the patient's larynx into the trachea to dispose the first bag in spaced relation to the larynx;

inflating the first bag to a first pressure via said first inflation line to seal with the trachea around the main tube;

positioning the second inflatable bag between the first bag and the larynx such that, when inflated, the second bag may contact or closely approach the first bag;

inflating the second bag to a second pressure lower than said first pressure to occupy substantially the entire space around the outside of the main tube between the first bag and the larynx and to be in contact with or closely approaching the first bag and applying suction to said suction line to remove secretions from a location between the first and second bags.

* * * * *